United States Patent [19]

Takago et al.

[11] Patent Number: 5,124,469
[45] Date of Patent: Jun. 23, 1992

[54] ORGANOSILICON COMPOUND

[75] Inventors: Toshio Takago; Shinichi Satoh; Masayuki Oyama, all of Annaka; Koichi Yamaguchi, Takasaki; Takashi Matsuda, Annaka, all of Japan

[73] Assignee: Shin-Etsu Chemical Co., Ltd., Tokyo, Japan

[21] Appl. No.: 515,416

[22] Filed: Apr. 27, 1990

[30] Foreign Application Priority Data

Apr. 28, 1989 [JP] Japan .................. 1-110196

[51] Int. Cl.$^5$ .......................... C07F 7/08; C07F 7/18
[52] U.S. Cl. .................................................. 556/438
[58] Field of Search ........................................ 556/438

[56] References Cited

U.S. PATENT DOCUMENTS 2,589,445  3/1951  Sommer ...................... 556/438 X
4,869,747  9/1989  Yoshioka et al. ............. 556/438 X

OTHER PUBLICATIONS

Noll, "Chemistry and Tech. of Silicones", Academic Press, N.Y. (1968), p. 167.
Bagant et al., "Organosilicon Compounds", Academic Press, N.Y. (1965), p. 180.

*Primary Examiner*—Paul F. Shaver
*Attorney, Agent, or Firm*—Oblon, Spivak, McClelland, Maier & Neustadt

[57] ABSTRACT

An organosilicon compound having the general formula (I):

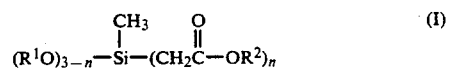

wherein $R^1$ represents the methyl group or the ethyl group, $R^2$ represent an alkyl group having from 1 to 4 carbon atoms, and n represents an integer of from 1 to 3. This compound is useful in preparing room temperature vulcaniazable organopolisiloxane compositions which have good storage stability, and release no smelly or corrosive condensation by-product on curing.

2 Claims, 4 Drawing Sheets

ORGANOSILICON COMPOUND

BACKGROUND OF THE INVENTION

1. Field Of The Invention

The present invention relates to a novel organosilicon compound, and in particular to an organosilicon compound useful as a curing agent for room temperature organopolysiloxane composition.

2. Description Of The Prior art

Room temperature vulcanizable (RTV) organopolysiloxane compositions used widely as one-pack type adhesives are prepared by adding a curing agent to an organopolysiloxane. The organopolysiloxane composition can be cured at room temperature only by discharging it in the air out of a tube or a cartridge; therefore it has the advantage of ease handling, and is used favorably in extensive fields including electrical/electronics, automotive and construction industries.

The RTV organopolysiloxane compositions are classified into addition-type ones and condensation-type ones according to their curing mechanism. For adhesives, condensation-type ones are mostly used. The condensationtype RTV organopolysiloxane composition is cured and adhered to a substrate while releasing a condensation byproduct inherent in the individual curing agent contained. That is, when a condensation-type RTV organopolysiloxane composition is exposed to the air, condensation takes place by moisture in the air to be cured, releasing a gas of e.g, acetic acid, butanoxime, methanol, butylamine, etc. These RTV organopolysiloxane compositions are known as deacetic acid type, deoximation type, dealcoholation type and deamination type ones, respectively, according to the condensation by-product.

Among the condensation-type RTV organopolysiloxane compositions, the deacetic acid type, deamination type and deoximation type ones have the disadvantage that toxic or corrosive, smelly gas is released on curing. On the other hand, the dealcoholation type ones have neither corrosiveness nor smell but have the disadvantage of poor storage stability.

In order to solve these problems, there has been developed an organosilicon compound containing an alkenyloxy group excellent in hydrolyzability, having the general formula:

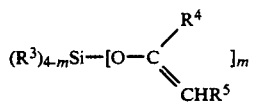

wherein $R^3$ represents a monovalent hydrocarbon group; $R^4$ and $R^5$ are each a hydrogen atom or a monovalent hydrocarbon group, and m represents an integer of from 1 to 4, and disclosed an RTV organopolysiloxane composition containing said organosilicon compound as a curing agent (Japanese Patent Pre-examination Publication (KOKAI) No. 44699/1979).

There has been also developed an organosilicon compound having both of a ketene acetal group and an alkenyloxy group as a curing agent, and an RTV organopolysiloxane composition containing this organosilicon compound is proposed (Japanese Patent Publication (KOKOKU) No. 20464/0988).

However, said organosilicon compound containing the alkenyloxy group disclosed in Japanese Patent Preexamination Publication (KOKAI) No. 44699/1979 has the disadvantages that it requires long time in synthesis and is expensive itself and that the compositions containing the organosilicon compound is susceptible to color change.

In the case of the composition disclosed in Japanese Patent Publication (KOKOKU) No. 20464/1988, because a silylketeneacetal is synthesized by 1,4-addition of Si-H group to $\alpha,\beta$-unsaturated ester, a smelly carboxylate ester having 2 or more carbon atoms, such as propionates, is released as a condensation by-product on curing.

SUMMARY OF THE INVENTION

Accordingly, an object of the present invention is to provide a novel organosilicon compound useful as a curing agent for RTV organopolysiloxane compositions and capable of giving RTV organopolysiloxane compositions that release no smelly or corrosive gas on curing and have good storage stability.

Thus, the present invention provides an organosilicon compound having the general formula (I)

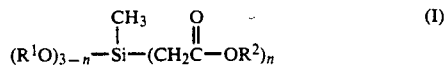

wherein $R^1$ represents the methyl group or the ethyl group, $R^2$ represents an alkyl group having from 1 to 4 carbon atoms, and n represents an integer of from 1 to 3.

The organosilicon compound of the present invention is a novel substance. Since this compound has high hydrolyzability, and reacts with the terminal Hydroxyl groups of an organopolysiloxane terminated with hydoxyl groups to release an acetate ester having neither smell nor corrosiveness; therefore it is markedly useful as an curing agent for RTV organopolysiloxane compositions. The composition obtained is not attended with smell or corrosiveness and has good storage stability; hence the composition can be used in extensive fields including as electrical/electronics, construction and automotive industries.

DETAILED DESCRIPTION OF PREFERRED EMBODIMENTS

Organosilicon compound

Figure 1:
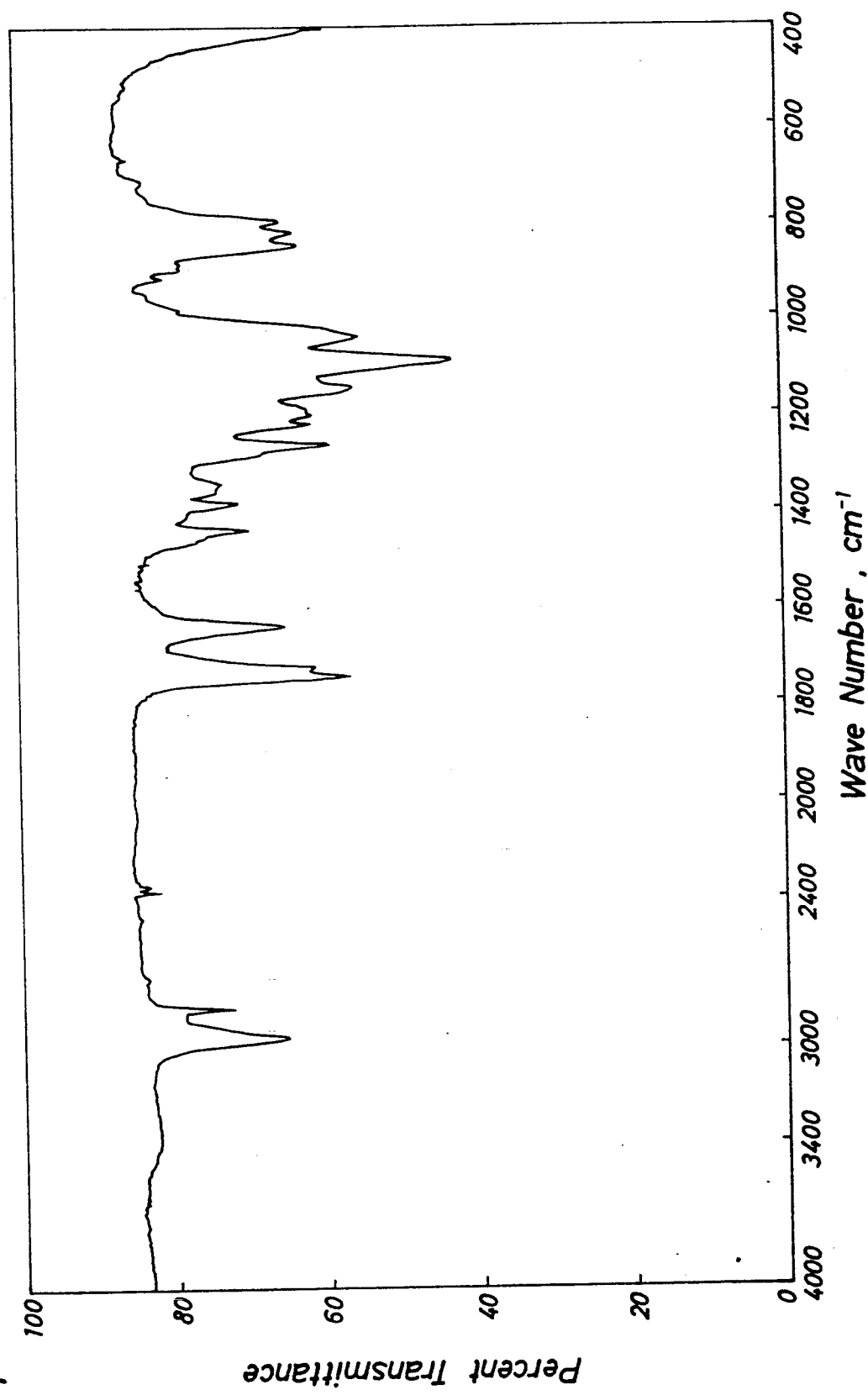
FIGS. 1 to 4 show IR spectra of organosilicon compounds of the present invention obtained in Examples 1 to 4, respectively.

In the general formula (I) representing the organosilicon compound of the present invention, $R^1$ represents the methyl group or the ethyl group, $R^2$ represents an alkyl group having from 1 to 4 carbon atoms, such as methyl, ethyl, propyl and butyl, and n represents an integer of from 1 to 3. Among the compounds of the general formula (I), as a curing agent for one-pack type RTV organopolysiloxane compositions, preferred are the compounds of the general formula wherein $R^1$ is the methyl group or the ethyl group. In view of readiness in isolation by distillation, $R^2$ in the general formula (I) is preferably the methyl group, ethyl group or isopropyl group. From viewpoint of readiness in synthesis, n in the general formula is preferably 1 or 2.

The compound of the general formula includes, for example, the compounds represented by the following formulas.

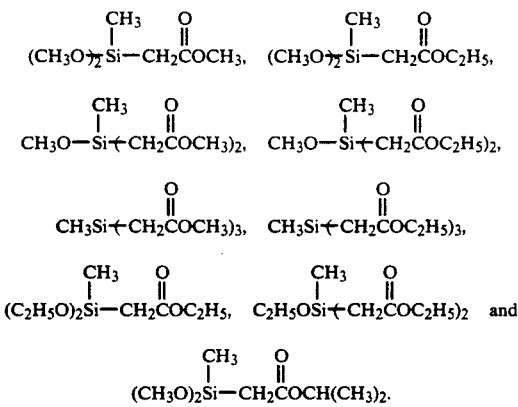

Production Process

The organosilicon compound of the present invention can be produced as described below, for example. That is, it can be produced by reacting a compound of the general formula (II):

$$(R^1O)_{3-n}-SiCl_n \quad \text{(II)}$$
(with CH$_3$ group on Si)

wherein R$^1$ and n are as defined above, with a compound having the general formula (III)

$$LiCH_2COR^2 \quad \text{(III)}$$

wherein R$^2$ is as defined above, thereby lithium chloride being eliminated. This reaction is normally carried out at −80° to −50° C. in an anhydrous aprotic non-polar solvent such as tetrahydrofuran, 1,4-dioxane and diethyl ether, under a dry inert gas atmosphere such as nitrogen and argon.

The compound of the general formula (III) used in the process can be prepared, for example, by reacting a secondary amine such as diisopropylamine with n-butyl lithium at −20° to 0° C. in an anhydrous aprotic non-polar solvent such as tetrahydrofuran, 1,4-dioxane and diethyl ether under dry inert atmosphere such as nitrogen and argon, to form a lithium salt of the secondary amine, which is then allowed to react with an acetate ester: CH$_3$COOR$^2$, where R$^2$ is as defined above, at −80° to −50° C.

Properties And Uses

The organosilicon compound of the general formula (I) exhibits a high hydrolyzability by virtue of the group Si-CH$_2$COOR$^2$ contained in the molecule. Therefore, in an one-pack type adhesive composition prepared by mixing the organosilicon compound as a curing agent with an organopolysiloxane terminated with hydroxyl groups at its both ends, etc., deacetate esterification proceeds by action of moisture in the air as expressed by the following equation:

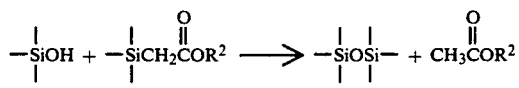

so that the composition is cured. The acetate ester released by this condensation has no smell or corrosiveness, the organosilicon compound of the general formula (I) is markedly useful as a curing agent for RTV organopolysiloxane compositions.

EXAMPLES

Example 1

In a 1 liter four-necked flask fitted with a stirring rod, dropping funnel, low temperature thermometer and condenser with a drying tube, were charged 266 g of anhydrous terahydrofuran and 40.4 g of diisopropylamine, and then the reaction mixture was cooled to 0° C. While the temperature of the reaction mixture was maintained at −10° to 0° C., 170.8 g of 15% n-butyl lithium solution in hexane was added dropwise thereto. After the addition, the reaction mixture was stirred at 0° C. for 15 minutes, followed by cooling to −78° C. with dry ice/acetone. Subsequently, after addition of 29.6 g of methyl acetate, the reaction mixture was stirred at −70° C. for 30 minutes, and then 126.0 g of methyldimethoxychlorosilane was added dropwise to the reaction mixture, while the temperature was being maintained at −70° C. or lower. The temperature of the reaction mixture was raised gradually to room temperature, and then the reaction mixture was subjected to filtration, followed by distillation to give 10.7 g of a distillate with a boiling point of 116° C./140 mmHg and a refractive index of 1.4134 at 25° C. (yield: 15.0%). The above procedure was conducted under dry nitrogen atmosphere. The distillate was subjected to measurement of $^1$H-NMR spectrum and IR spectrum, and GC/MS analysis; the results obtained are given below.

From the results, the product was identified as the compound having the following structure.

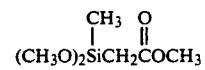

$^1$H-NMR spectrum
Solvent: CCl$_4$;
Internal standard: TMS (tetramethylsilane).
δ(ppm): 0.06 (s, Si—CH$_3$, 3H);
1.28 (s, Si—CH$_2$, 2H);
3.52 (s, SiO—CH$_3$, 6H);
3.54 (s, CO—CH$_3$, 3H);
IR spectrum
As shown in FIG. 1. The absorption band due to carbonyl group (C=O) was recognized at 1,740 cm$^{-1}$.
GC/MS
Parent peak: 178 (molecular weight:178.3).

Example 2

In a 1 liter four-necked flask fitted with a stirring rod, dropping funnel, low temperature thermometer and condenser with a drying tube, were charged 178 g of anhydrous terahydrofuran and 30.4 g of diisopropylamine, and then the reaction mixture was cooled to 0° C. While the temperature of the reaction mixture was maintained at −10° to 0° C., 128.0 g of 15% n-butyl lithium solution in hexane was added dropwise thereto. After the addition, the reaction mixture was stirred at 0° C. for 15 minutes, followed by cooling to −78° C. with dry ice/acetone. Subsequently, after addition of 26.5 g of ethyl acetate, the reaction mixture was stirred at −70° C. for 30 minutes, and then 90.0 g of methyldimethoxychlorosilane was added dropwise to the reaction mixture, while the temperature was being maintained at −70° C. or lower. The temperature of the reaction mixture was raised gradually to room temperature, and then the reaction mixture was subjected to filtration, followed by distillation to give 7.1 g of a distillate with a boiling point of 95° C./49 mmHg and a refractive index of 1.4156 at 25° C. (yield: 12.3%). The above procedure was conducted under dry nitrogen atmosphere. The distillate was subjected to measurement of $^1$H-NMR spectrum and IR spectrum, and GC/MS analysis; the results obtained are given below.

From the results, the product was identified as the compound having the following structure.

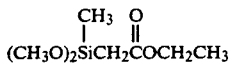

Figure 2:
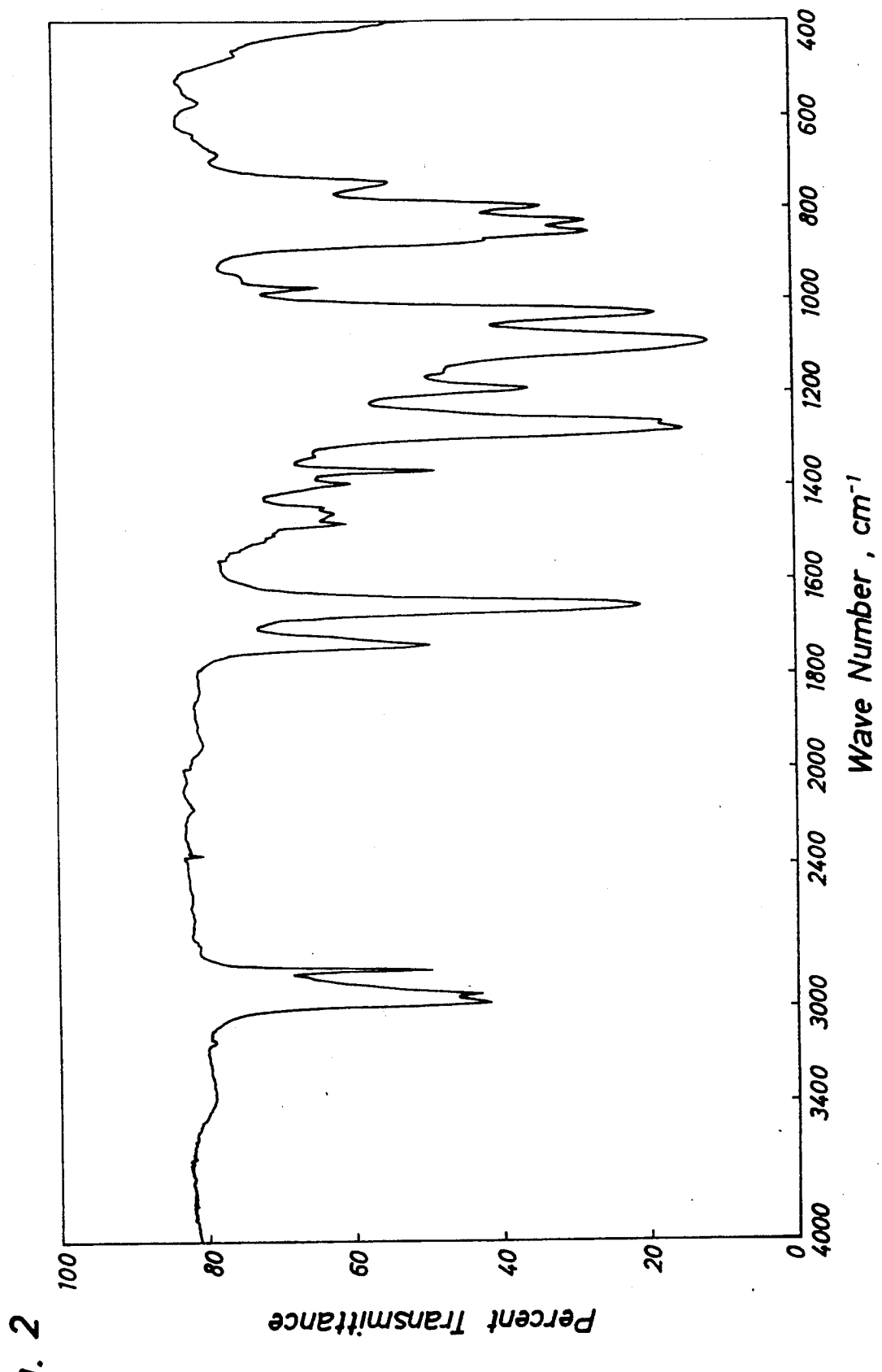

$^1$H-NMR spectrum
Solvent: CCl$_4$;
Internal standard: TMS (tetramethylsilane.
δ(ppm): 0.05 (s, Si—CH$_3$, 3H); 1.11 (s, C—CH$_3$, 3H); 1.70 (s, Si—CH$_2$, 2H); 3.56 (s, SiO—CH$_3$, 6H); 3.96 (s, CO—CH$_2$, 2H);
IR spectrum
As shown in FIG. 2. The absorption band due to carbonyl group (C=O) was recognized at 1,740 cm$^{-1}$.
GC/MS
Parent peak: 192 (molecular weight: 192.3).

Example 3

In a 2 liter four-necked flask fitted with a stirring rod, dropping funnel, low temperature thermometer and condenser with a drying tube, were charged 655.5 g of anhydrous terahydrofuran and 101.2 g of diisopropylamine, and then the reaction mixture was cooled to 0° C. While the temperature of the reaction mixture was maintained at −10° to 0° C., 343.8 g of 15% n-butyl lithium solution in hexane was added dropwise thereto. After the addition, the reaction mixture was stirred at 0° C. for 15 minutes, followed by cooling to −78° C. with dry ice/acetone. Subsequently, after addition of 88.1 g of ethyl acetate, the reaction mixture was stirred at −70° C. for 30 minutes then 72.5 g of methylmethoxydichlorosilane was added dropwise to the reaction mixture, while the temperature was being maintained at −70° C. or lower, followed by stirring for 1 hour. Then, 168.2 g of trimethylchlorosilane was added thereto. Thereafter, the temperature of the reaction mixture was raised gradually to room temperature, and then the reaction mixture was subjected to filtration, followed by distillation to give 31.7 g of a distillate with a boiling point of 105° C./4 mmHg and a refractive index of 1.4332 at 25° C. (yield: 12.8%). The a was conducted under dry nitrogen atmosphere. The distillate was subjected to measurement of $^1$H-NMR spectrum and IR spectrum, and GC/MS analysis; the results obtained are given below.

From the results, the product was identified as the compound having the following structure.

Figure 3:
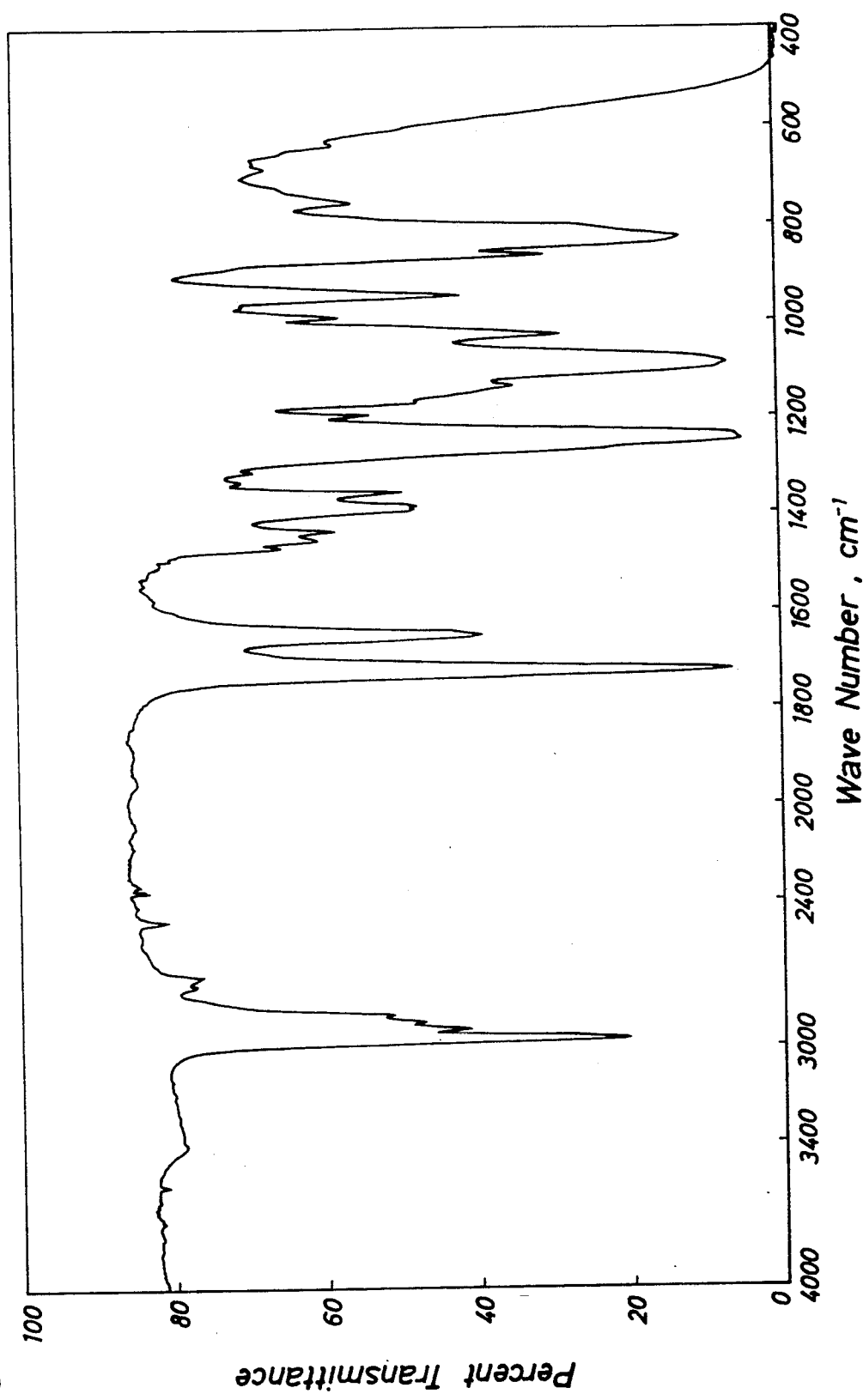

$^1$H-NMR spectrum
Solvent: CCl$_4$;
Internal standard: TMS (tetramethylsilane).
δ(ppm) : 0.06 (s, Si—CH$_3$, 3H);
1.16 (t, C—CH$_3$, 6H);
1.89 (s, Si—CH$_2$, 4H);
3.50 (s, SiO—CH$_3$, 3H);
3.71 (q, CO—CH$_2$, 4H);
IR spectrum
As shown in FIG. 3. The absorption band due to carbonyl group (C=O) was recognized at 1,721 cm$^{-1}$.
GC/MS
Parent peak: 248 (molecular weight: 248.3).

Example 4

In a 2 liter four-necked flask fitted with a stirring rod, dropping funnel, low temperature thermometer and condenser with a drying tube, were charged 667.0 g of anhydrous terahydrofuran and 101.2 g of diisopropylamine, and then the reaction mixture was cooled to 0° C. While the temperature of the reaction mixture was maintained at −10° to 0° C., 427.0 g of 15% n-butyl lithium solution in hexane was added dropwise thereto. After the addition, the reaction mixture was stirred at 0° C. for 15 minutes, followed by cooling to −78° C. with dry ice/acetone. Subsequently, after addition of 88.0 g of ethyl acetate, the reaction mixture was stirred at −70° C. for 30 minutes, and then 119.4 g of methyltrichlorosilane was added dropwise with the temperature of the reaction mixture being maintained at −70° C. or lower. Thereafter, 119.4 g of trimethylchlorosilane was added dropwise to the reaction mixture. The temperature of the reaction mixture was raised gradually to room temperature, and then the reaction mixture was subjected to filtration, followed by distillation to give 22.5 g of a distillate with a boiling point of 115° C./1 mmHg and a refractive index of 1.4298 at 25° C. (yield: 8.6%). The above procedure was conducted under dry nitrogen atmosphere. The distillate was subjected to measurement of $^1$H-NMR spectrum and IR spectrum, and GC/MS analysis; the results obtained are given below.

From the results, the product was identified as the compound having the following structure.

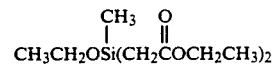

Figure 4:
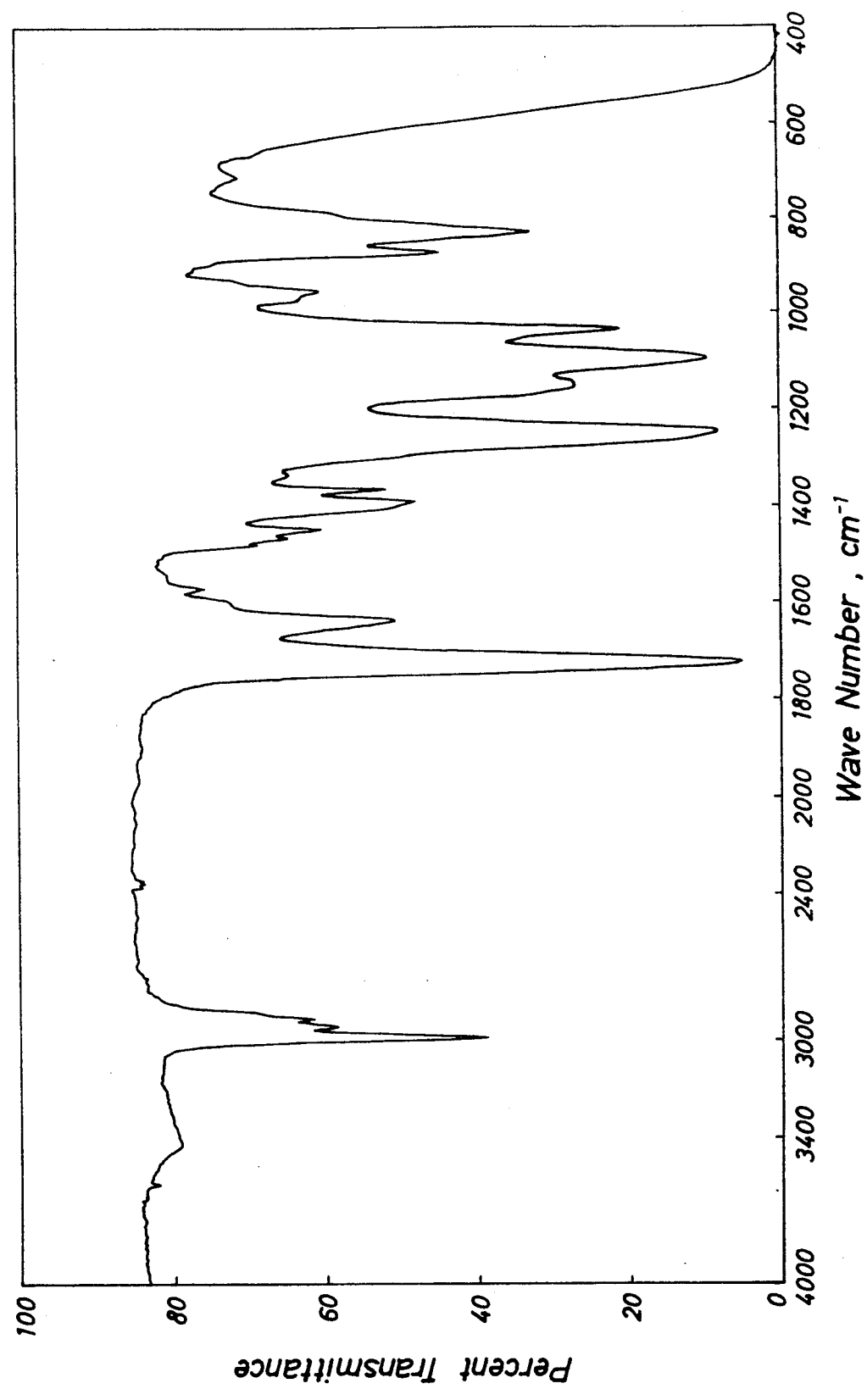

$^1$H-NMR spectrum
Solvent: CCl$_4$;
Internal standard: TMS (tetramethylsilane).
δ(ppm): 0.28 (s, Si—CH$_3$, 3H);
1.26 (t, C—CH$_3$, 9H);
2.00 (s, Si—CH2, 4H);
4.07 (q, O—CH$_2$, 6H);
IR spectrum
As shown in FIG. 4. The absorption band due to carbonyl group (C=O) was recognized at 1,720 cm$^{-1}$.
GC/MS
Parent peak: 262 (molecular weight: 262.4).

We claim:
1. An organosilicon compound having the general formula (I):

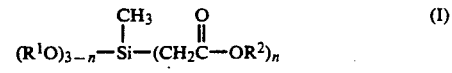

wherein R$^1$ represents the methyl group or the ethyl group, R$^2$ represents an alkyl group having from 1 to 4 carbon atoms, and n represents an integer of from 1 to 3.
2. The compound according to claim 1, wherein in the general formula (I) R$^1$ represents the methyl group or the ethyl group, R$^2$ represents the methyl group, the ethyl group or the isopropyl group, and n represents an integer of 1 or 2.

* * * * *